(12) United States Patent
Yuuki

(10) Patent No.: US 10,791,921 B2
(45) Date of Patent: Oct. 6, 2020

(54) OPHTHALMOLOGIC EXAMINATION APPARATUS

(71) Applicant: Shinko Seiki Co., LTD, Kobe (JP)

(72) Inventor: Hiroshi Yuuki, Kobe (JP)

(73) Assignee: Shinko Seiki Co., Ltd, Kobe (JP)

(*) Notice: Subject to any disclaimer, the term of this patent is extended or adjusted under 35 U.S.C. 154(b) by 142 days.

(21) Appl. No.: 16/099,238

(22) PCT Filed: May 13, 2016

(86) PCT No.: PCT/JP2016/064270
§ 371 (c)(1),
(2) Date: Nov. 6, 2018

(87) PCT Pub. No.: WO2017/195347
PCT Pub. Date: Nov. 16, 2017

(65) Prior Publication Data
US 2019/0209004 A1 Jul. 11, 2019

(51) Int. Cl.
*A61B 3/02* (2006.01)
*A61B 3/024* (2006.01)
(Continued)

(52) U.S. Cl.
CPC .......... *A61B 3/024* (2013.01); *A61B 3/0008* (2013.01); *A61B 3/032* (2013.01)

(58) Field of Classification Search
CPC ......... A61B 3/102; A61B 3/024; A61B 3/032; A61B 3/08; A61B 3/09
(Continued)

(56) References Cited

U.S. PATENT DOCUMENTS 6,141,092 A * 10/2000 Kim .................. G01J 1/00
356/214
2010/0182570 A1 7/2010 Matsumoto et al.
2012/0236262 A1 9/2012 Johansson

FOREIGN PATENT DOCUMENTS

EP 2165645 A1 3/2010
JP 2006340755 A 12/2006
(Continued)

OTHER PUBLICATIONS

Japan Patent Office, PCT International Search Report issued in corresponding PCT International Application No. PCT/JP2016/064270, dated Jun. 21, 2016, pp. 1-2, including English translation.
(Continued)

*Primary Examiner* — Hung X Dang
(74) *Attorney, Agent, or Firm* — Duane Morris LLP

(57) ABSTRACT

To realize highly reliable examination by means of an apparatus free of troublesome adjustment of which structure as a whole is simple. The examination contributes to early discovery of glaucoma in particular. Light emitted from a matrix-type light-emitting diode unit 12 is projected onto an eye to be examined through a liquid crystal shutter 16 and a main optical system 14. The matrix-type light-emitting diode unit 12 includes a plurality of light-emitting diodes devices 12b, 12b, 12b, of the same specifications arranged in a matrix array. The light-emitting diode devices 12b, 12b, 12b are independently controlled to form an image for use in the examination. The image includes a circular visual target 100a and a background 100b which is a remaining portion of the image. The visual target 100a flickers generally sinusoidally at a frequency between 1 Hz and 200 Hz. With this arrangement, highly reliable examination contributing to early discovery of glaucoma is realized. The struc-
(Continued)

ture of the apparatus as a whole is simple, and no troublesome adjustments are required.

7 Claims, 12 Drawing Sheets

(51) Int. Cl.
*A61B 3/032* (2006.01)
*A61B 3/00* (2006.01)
(58) Field of Classification Search
USPC ....... 351/222, 221, 224, 237, 239, 240, 245, 351/246
See application file for complete search history.

(56) References Cited

FOREIGN PATENT DOCUMENTS

WO     2009001458 A1    12/2008
WO     2014167688 A1    10/2014

OTHER PUBLICATIONS

Search Report issued in connection with corresponding European Patent Application No. 16901695.3, dated Jul. 4, 2019, 6 pages.

\* cited by examiner

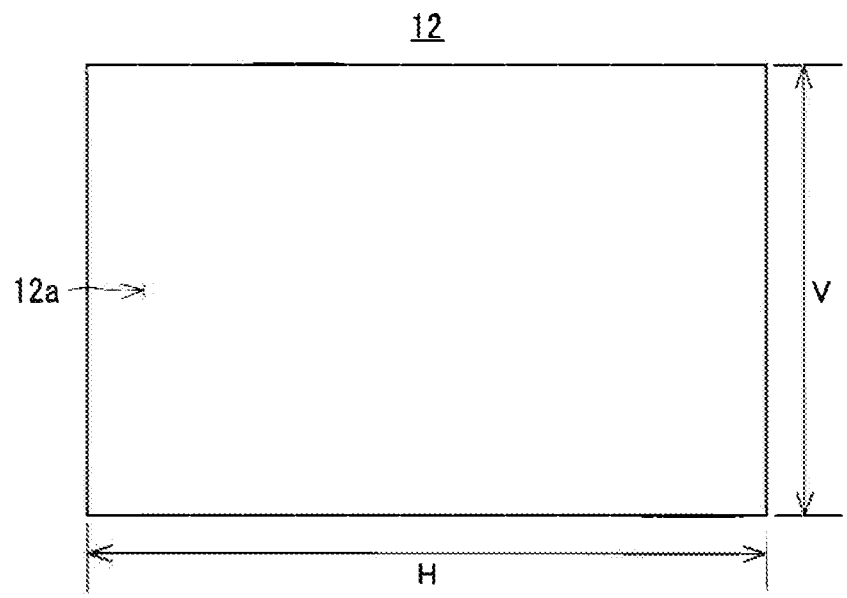
Fig.2A  Entire Viewing LED Unit (Light Emitting Surface)
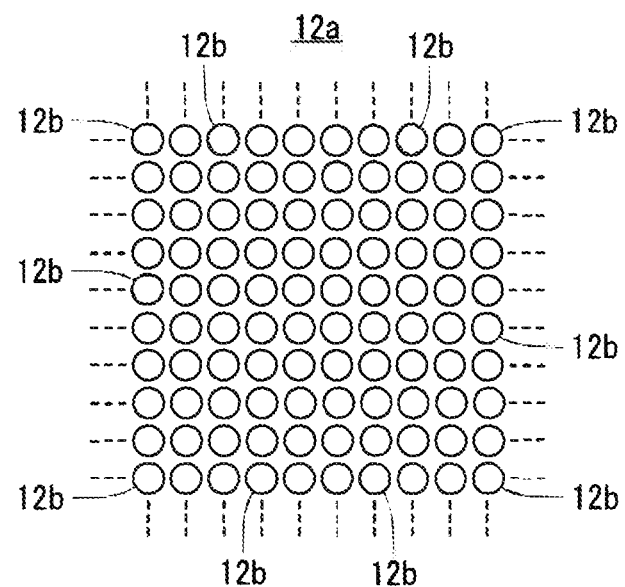
Fig.2B  Enlarged View of Portion of Fig.2A

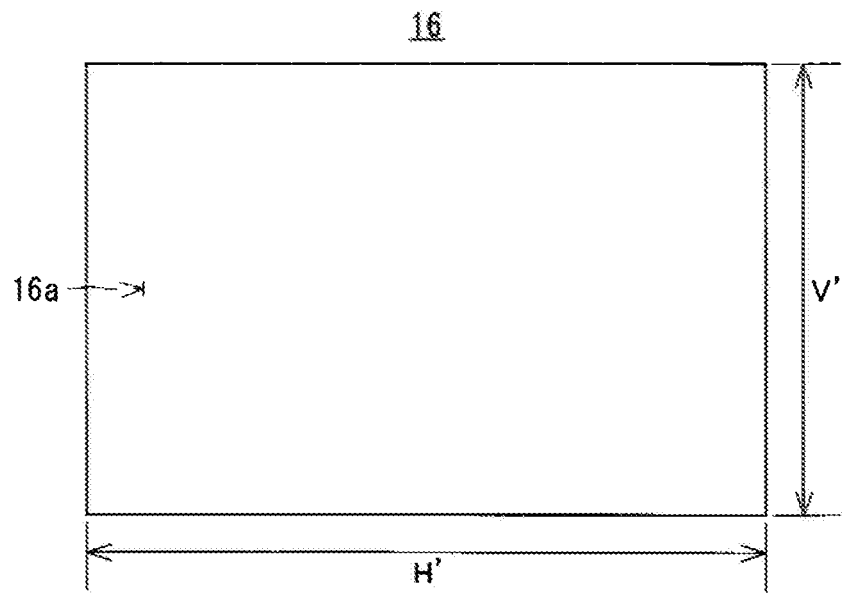
Fig.3A Entire View of Liquid Crystal Shuter(Light-Valve Surface)
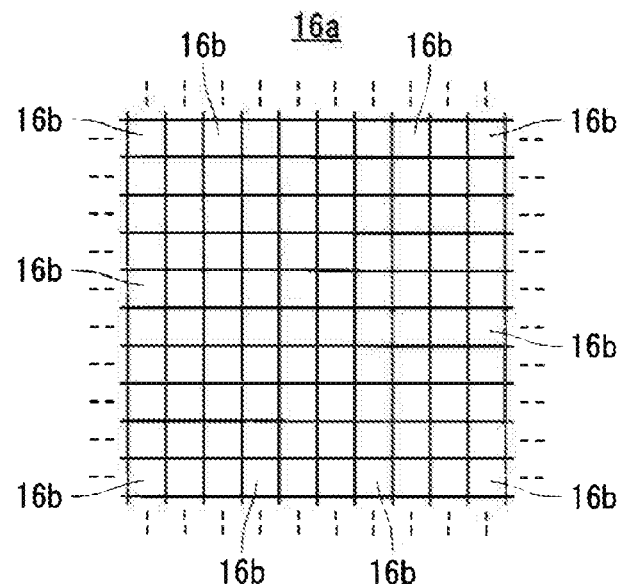
Fig.3B Enlarged View of Portion of Fig.3A

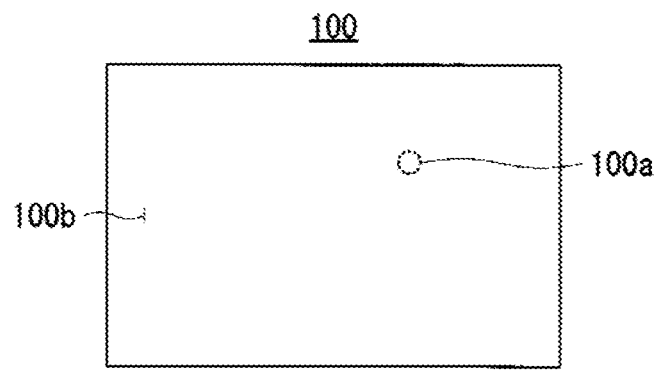
Fig. 7A Visual Target Presented with Highest Brightness
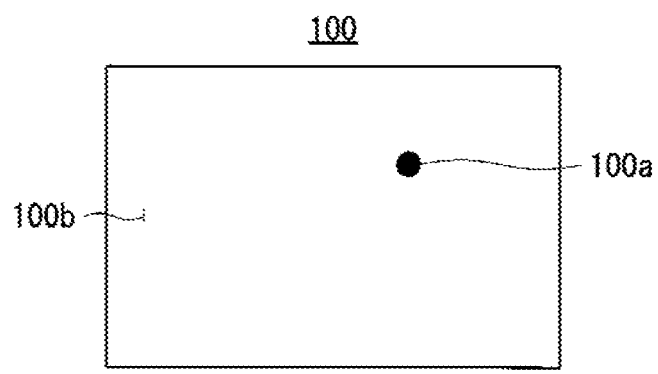
Fig 7B Visual Target Presented with Lowest Brightness
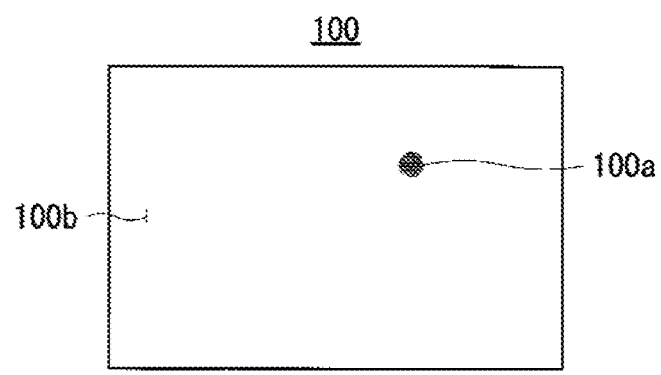
Fig 7C Visual Target Presented with Intermediate Brightness

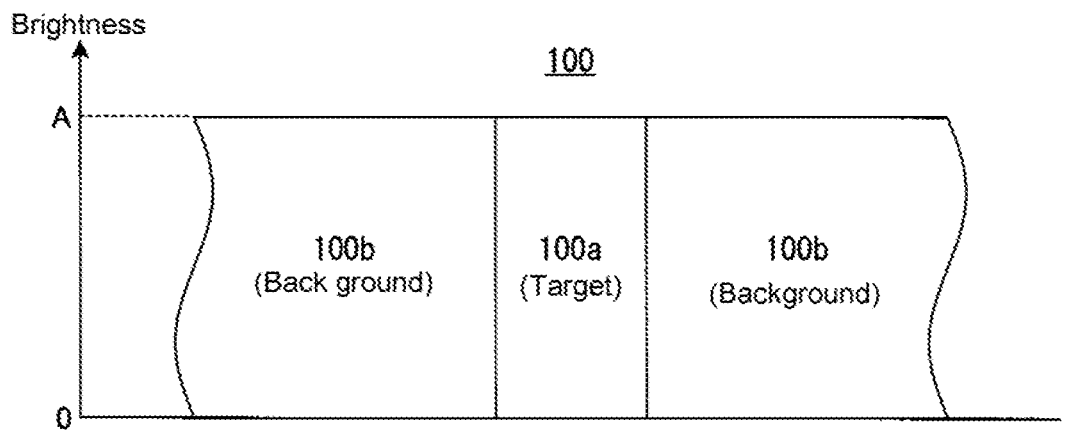
Fig.9A Visual Target Presented with Highest Brightness
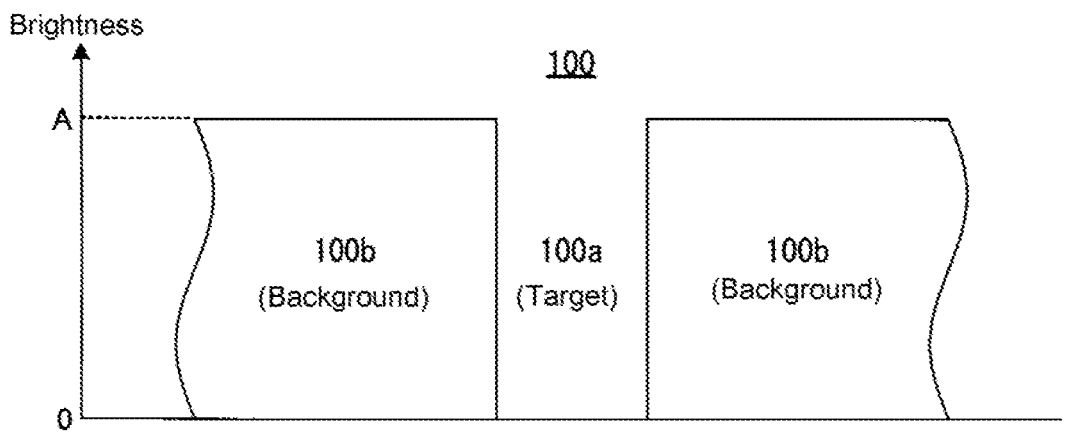
Fig.9B Visual Target Presented with Lowest Brightness
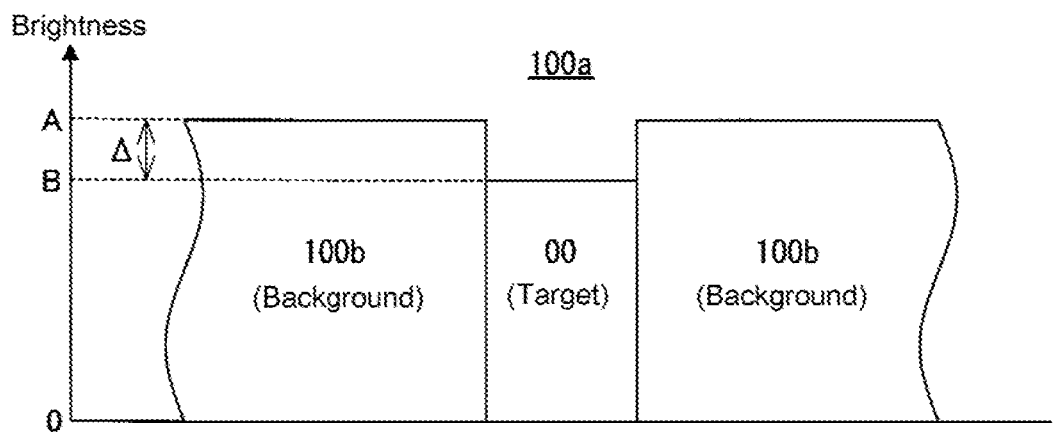
Fig.9C Visual Target seen to be Presented with Constant Brightness Lower than Background

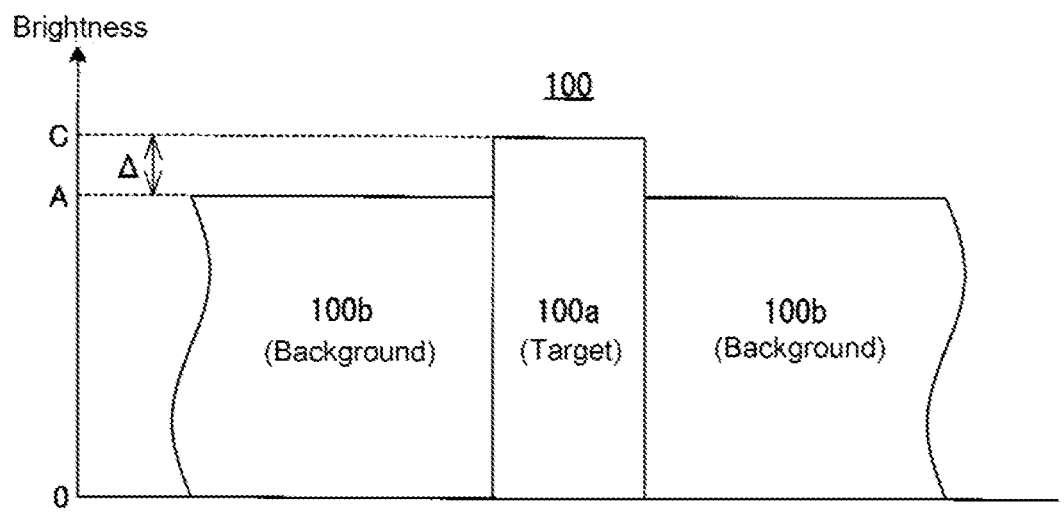
Fig.12A Visual Target Presented with Highest Brightness
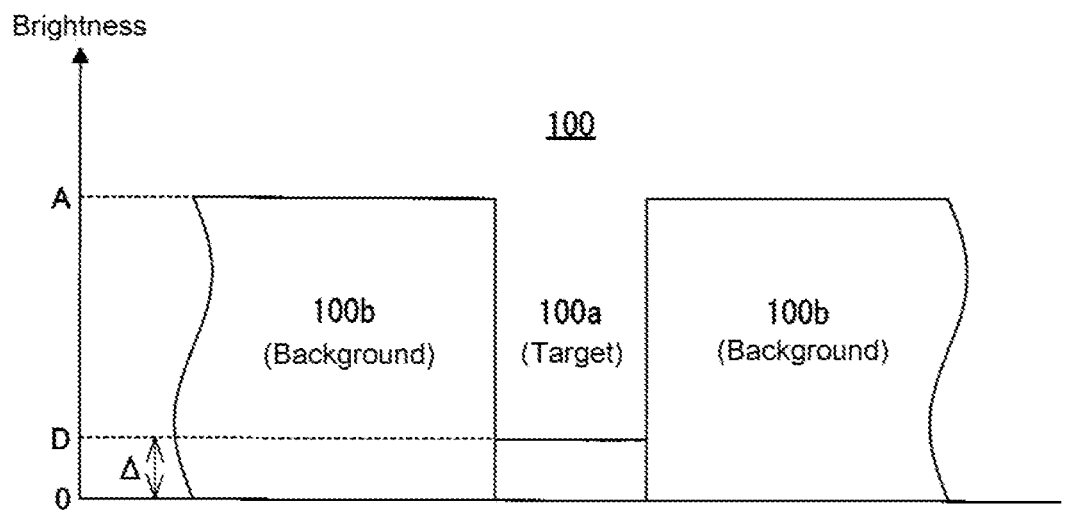
Fig.12B Visual Target Presented with Lowest Brightness

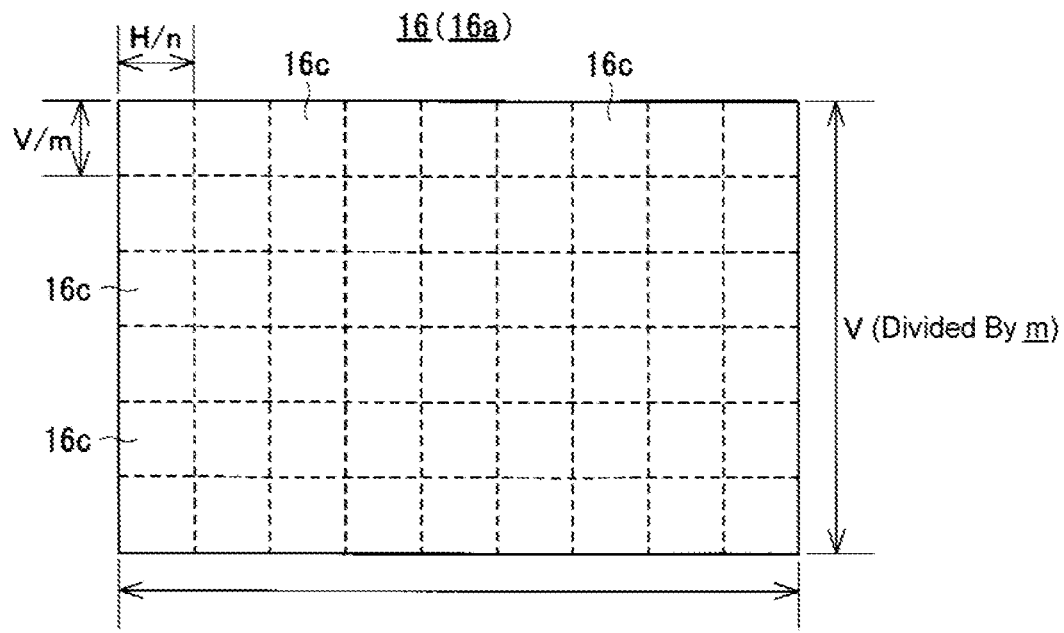
Fig.13A Entire View of LED Unit (Light-Emitting Surface) Divided into Plural Blocks
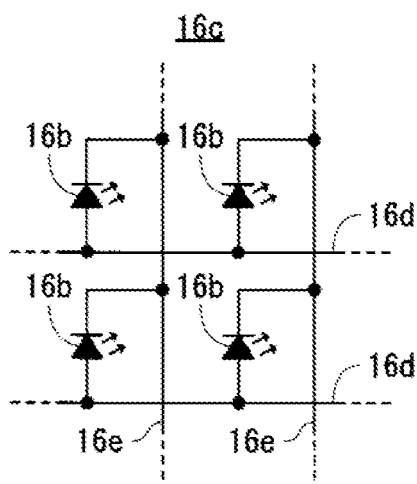
Fig.13B Electrical Arrangement of Portion of Unit Shown in Fig.13A

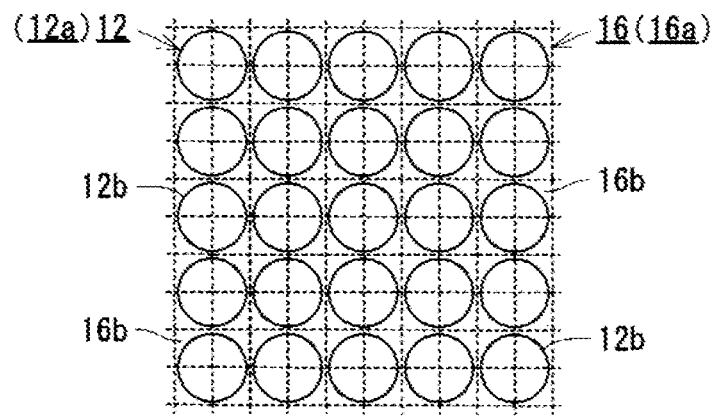
Fig.14A One LED Device for 2X2 Liquid Crystal Pixels
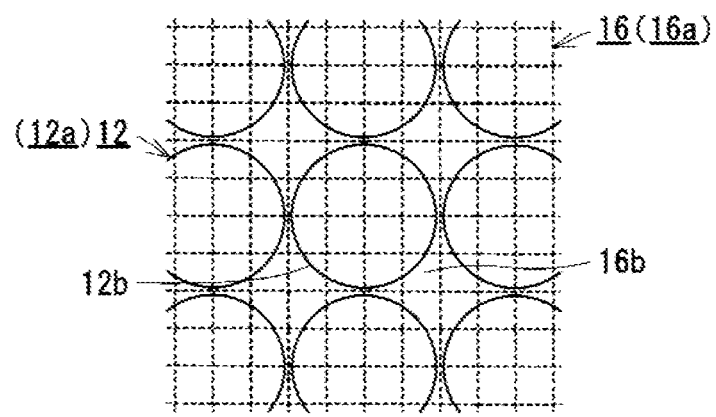
Fig.14B One LED Device for 4X4 Liquid Crystal Pixels
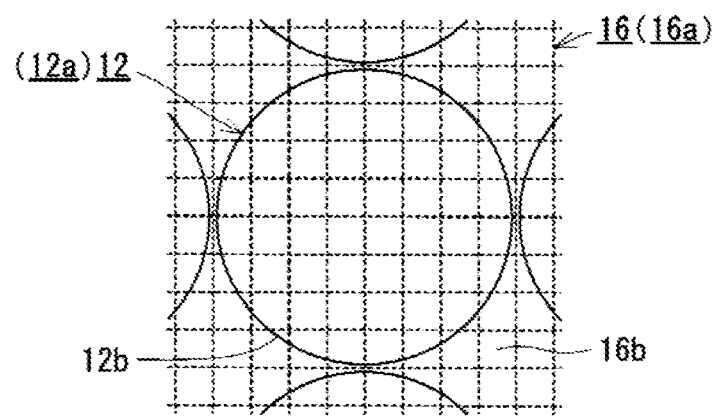
Fig.14C One LED Device for 8X8 Liquid Crystal Pixels

OPHTHALMOLOGIC EXAMINATION APPARATUS

TECHNICAL FIELD

This invention relates to an ophthalmologic examination apparatus and, more particularly, to an ophthalmologic examination apparatus which presents an image for examination containing a blinking visual target to an eye to be examined and examines the eye based on how the eye recognizes the target.

BACKGROUND ART

An example of ophthalmologic examination apparatuses of this type is shown in Patent Literature 1. According to the technique disclosed in Patent Literature 1, the apparatus is provided with visual target light generating means for generating target light for forming a visual target in an image to be presented to an eye to be examined, background light generating means for generating background light for forming a background occupying an area of said image excluding the visual target, and combining means for combining the target light and the background light together and projecting the resultant light to the eye to be examined. The visual target light and the background light are each unpolarized light. The combining means combines the target light and the background light keeping the light unpolarized.

Specifically, there are provided a light source of light for presenting a visual target, a visual target presenting collimator lens for collimating unpolarized light emitted from the visual target presenting light source, and a visual target presenting liquid crystal shutter having an incident surface onto which light collimated by the collimator lens is incident. The visual target presenting liquid crystal shutter forms on the incident surface thereof a shutter pattern in accordance with a visual target presenting shutter control signal applied from a liquid crystal controller whereby a part of the incident surface area is a translucent region and the rest of the incident surface area is a light-blocking region. In addition, there are provided a light source of light for presenting a background, a background presenting collimator lens for collimating unpolarized light from the background presenting light source, and a background presenting liquid crystal shutter having an incident surface onto which light collimated by the background presenting collimator lens is incident. In response to a background presenting shutter control signal provided by the liquid crystal controller, the background presenting liquid crystal shutter forms, on the incident surface thereof, a shutter pattern exactly reverse to the shutter pattern formed by the visual target presenting liquid crystal shutter. The light portions which have passed through the respective liquid crystal shutters (or their respective translucent regions) are combined by combining means, e.g. a half prism or beam splitter, and the resultant light is projected onto the eye to be examined. The background presenting light source emits light with a constant brightness level. On the other hand, the visual target presenting light source alternates between a first state in which it emits light with the same level as the background presenting light source and a second state in which it emits no light. In other words, the visual target presenting light source blinks. As a result, the eye to be examined is exposed alternately to an image of brightness level uniform over the entire visual field and to an image having a portion which is dark or missing. In other words, an image including a visual target which corresponds to the missing portion and blinks, and a background, a region excluding the visual target having a brightness level which is constant and same as that of the visual target when the visual target is brightest, is presented to the eye to be examined.

In other words, the visual target is presented to the eye to be examined with a brightness level same as or lower than that of the background. Accordingly, the amount of light incident onto the eye to be examined when the visual target is presented to the eye can be prevented from increasing, resulting in suppression of the stimulus to the eye (or the retina). This is very important in improving the reliability of subjective examinations (examinations based on self-recognition), e.g. visual field examination. For example, in a visual field examination, a visual target is displayed at various locations in the visual field of a person to be examined (or an eye to be examined). The person with the eye being examined is instructed to fix the eye on a predetermined fixed point (usually displayed at a location in front of the eye) and to give a signal by, for example, pressing a button, when the eye recognizes the visual target. Let it be assumed that the person being examined lacks a portion of the visual field and the visual target is displayed at the missing visual field portion. If it is arranged that a pitch-black background is displayed and a bright visual target displayed on the pitch-black background, or, in other words, the brightness level of the visual target is higher than that of the background, the person having his or her eye examined could wrongly think as if he or she recognized the visual target, which is caused by stimulation by the visual target displayed brighter than the background, although he or she actually cannot recognize such visual target. This could lower the reliability of the examination. In contrast according to the above-described prior art, since the visual target is presented to the eye to be examined with brightness lower than the background, stimulation to the eye of the above-described type can be suppressed, and, accordingly, false recognition can be prevented. Thus, eye examination can be realized with a higher reliability.

In addition, the resultant light projected onto the eye to be examined is unpolarized light as natural light. Then, in comparison with a case in which resultant light presented to the eye to be examined is polarized light, a more reliable examination can be made. Specifically, when the resultant light, which is polarized light, is projected to the eye to be examined, the image (particularly the visual target) looks differently to the eye to be examined, depending on the angle of incidence onto the eye. The prior art is no affected by such polarization, which greatly contributes to the realization of highly reliable examination.

According to the described prior art, the visual target presenting light source blinks and, therefore, the visual target blinks. More specifically, the visual target presenting light source gently blinks sinusoidally, and, accordingly, the visual target also gently blinks sinusoidally. In comparison with blinking of the visual target in, for example, a rectangular waveform (or, so to say, in an ON-OFF manner), the gentle blinking of the visual target or, in other words, a gradual change of the brightness of the visual target, can further reduce stimulation of the eye to be examined, in comparison to stimulation by a rapid change of brightness of the visual target. This may promise realization of more reliable ophthalmologic examination and, accordingly, contribution to early discovery and treatment of glaucoma. The visual target blinking frequency is arbitrarily controlled to a required frequency in a range of from 1 Hz to 120 Hz, for example, to accommodate the system to various conditions, such as various differences among people to be examined.

As describe above, according to the described prior art, the image for the examination purpose (hereinafter sometimes referred to "examination image") presented to the eye to be examined (hereinafter referred sometimes to simply "the eye") includes the visual target and the remaining region or background. The visual target and the background are generated by separate means, namely, the visual target light generating means and the background light generating means. Accordingly, it is necessary that the positional relationship between the visual target light generating means and the background light generating means be proper, but it is very difficult to realize such proper positional relationship. More specifically, it is necessary to realize a proper relation in position between the path (optical path) of the visual target light extending from the visual target presenting light source through the visual target presenting collimator lens and the visual target presenting liquid crystal shutter to the half prism or beam splitter acting as the combining means, and the path of the background light extending from the background presenting light source through the background presenting collimator lens and the background presenting liquid crystal shutter to the half prism or beam splitter. It is particularly very difficult to adjust the positional relationship between the respective liquid crystal shutters. Furthermore, the target and the background may have variations in brightness and color etc. due to imbalance of optical characteristics etc. between the optical paths of the visual target light and the background light. It is also troublesome to correct such differences. In addition, the system as a whole requires, in addition to the target light generating means and the background light generating means, the combining means such as the half prism. Accordingly, it is desired to further simplify the system arrangement.

Another prior art is disclosed in, for example, Patent Literature 2. The second prior art disclosed in Patent Literature 2, there are provide one light source means, light valve means having an incidence surface onto which light generated from the light source means is incident, and light valve control means for controlling the light valve means. The light valve means may be a liquid crystal shutter, for example, which modulates the light incident on the incidence surface thereof and projects the modulated light onto the eye to be examined, whereby the examination image including the target is presented to the eye. The light valve control means controls the light valve means in such a manner that the visual target in the examination image is formed by light incident on a portion of the incidence surface of the light valve means and that the background in the examination image excluding the target is formed by light incident on the remaining portion of the incidence surface of the light valve means.

More specifically, the light source means is a white light emitting diode emitting light of a predetermined brightness. The light emitted by the white light emitting diode is collimated by a collimator lens and, thereafter, projected onto the incidence surface of the liquid crystal shutter acting as the light valve means. The liquid crystal shutter alternately forms, on its incidence surface, shutter patterns, namely, a first pattern in which the entire incidence surface is light-transmissive and a second pattern in which a part of the incidence surface is light-blocking region, in accordance with a shutter control signal provided by a liquid crystal controller acting as the light valve control means. In other words, the said part of the incidence surface of the liquid crystal shutter alternately changes between the transmissive state and the light-blocking state, and the remaining portion of the incidence surface of the liquid crystal shutter remains light-transmissive. The light passing through the incidence surface of the liquid crystal shutter is projected through a magnifying optical system to the eye. As a result, an image including a visual target which corresponds to the said part of the incidence surface and blinks, and a background which corresponds to the remaining portion of the incidence surface of the liquid crystal shutter and has brightness the same as that of the target when it is brightest, is presented to the eye to be examined.

According to the second prior art, an examination image similar to the one of the first prior art disclosed in the above-discussed Patent Literature 1 is presented to the eye. According to the first prior art, however, the target light generating means, the background light generating means and the combining means are used for the presentation of the examination image, and separate means are used as the target light generating means and the background light generating means. On the other hand, according to the second prior art, the single light source means, the single light valve means and the single light valve control means are used to present the examination image to the eye to be examined. In other words, the means are used in common for the target and the background. According to the first prior art, the adjustment of the relative positions of the target light generating means and the background light generating means is required, while the second prior art does not require such adjustment. Further, while, according to the first prior art, there may be produced difference in brightness, color etc. between the target and the background due to imbalance in optical characteristics of the target light optical path and the background light optical path, no such difference is seen and, therefore, no adjustment of such difference is required according to the second prior art. In addition, the second prior art does not require combining means as required for the first prior art. Thus, the structure of the system as a whole can be simplified.

As in the first prior art, the visual target is arranged to blink in a sinusoidal manner (i.e. along an approximately sinusoidal wave form) also according to the second prior art. Accordingly, the alteration of the first and second patterns of the shutter pattern formed on the incidence surface of the liquid crystal shutter is a sinusoidal manner so that the transmissivity of the regions of the incidence surface of the liquid crystal shutter corresponding to the target changes gently in a sinusoidal manner. The blinking period of the target is controllable to one within a range of from 5 ms to 1 s, or, in other words, the blinking frequency of the target can be changed to a desired one of the frequencies from 1 Hz to 200 Hz.

The liquid crystal shutter serving as light valve means of the second prior art is one having what is called a FHD (Full High Definition) screen resolution with the number of pixels (or resolution) in the horizontal direction of, for example, 1920, and the number of pixels (or resolution) in the vertical direction of, for example, 1080. Although not specifically described in the Patent Literature 2, it utilizes a transmissive monochrome liquid crystal panel for liquid crystal projector. It is well known that liquid crystal panels for use in display devices, including a liquid crystal projector have predetermined screen rewriting speed or refresh rate, which is usually around 60 Hz, and about 240 Hz at the highest. Assuming that, as the liquid crystal shutter of the second prior art, a liquid crystal panel having a refresh rate of 240 Hz is used, the refresh frequency of the shutter pattern formed on the incidence surface of the liquid crystal shutter is 240 Hz. This means that, in case that the visual target blinks in a rectangular wave manner, for example, the blinking frequency of the target is 120 Hz (=240 Hz/2) at the highest. If, on the other hand, the target sinusoidally blinks gently as described above, for example, the highest blinking frequency of the target is far lower than the frequency of 120 Hz. With such blinking frequency, it is not possible to realize an examination of higher reliability which can contribute to early detection of glaucoma.

PRIOR ART LITERATURE

Patent Literature

Patent Literature 1: WO 2009/001458
Patent Literature 2: WO2014/167688

SUMMARY OF INVENTION

Technical Problem

As described above, according to the first prior art, while reliable examination which contributes to early discovery of glaucoma can be realized, it has problems of requiring very troublesome adjustments and having complicated structures. On the other hand, the second prior art is free from the problems seen in the first prior art, but it cannot realize reliable examination which can contribute to early discovery of glaucoma.

In view of these facts, an object of the present invention is to provide a novel ophthalmologic examination apparatus which requires no troublesome adjustments and has a simple entire structure, and still, can realize highly reliable examination that can contribute to early discover of glaucoma.

Means to Solve the Problems

To achieve this object, according to the present invention, an ophthalmologic examination apparatus which presents, to an eye to be examined, an image for use in ophthalmologic examination containing a flickering visual target and examines the eye based on how the eye recognizes the target, includes light-emitting means and light-emission control means. The light-emitting means includes a plurality of light-emitting devices. The light-emitting devices are of the same specifications and are two-dimensionally arranged to form an image to be presented to the eye to be examined. The light-emitting devices emit light of brightness controllable independently from and in parallel with each other. The light-emission control means controls the brightness of the light-emitting devices of the light-emitting independently from and in parallel with each other. More specifically, the light-emission control means performs control in such a manner that a part of the light-emitting devices flicker to form a visual target in the examination image whereas the remaining light-emitting devices emit light of a constant brightness to thereby provide the remainder of the examination image, or, in other words, a background.

Thus, according to the present invention, the examination image to be presented to the eye to be examined includes a visual target and a background. This image, including the target and the background, is formed by the plurality of two-dimensionally arranged light-emitting devices of the light-emitting means. Specifically, some of the light-emitting devices emit light of varying brightness (i.e. brightens and darkens) to form the target, and the remaining light-emitting devices emit light at a constant brightness to form the background. In other words, the target is formed by a part of the two-dimensionally arranged light-emitting devices, and the background is formed by the remaining ones of the light-emitting devices. According to the aforementioned first prior art, for example, the target and the background are formed by separate means and, therefore, the relation in position of the target and the background must be adjusted. However, according to the present invention, no such adjustment is required at all. Furthermore, since the light-emitting devices used in the present invention are of the same specifications, and, accordingly, their properties are (basically) the same. According to the first prior art, for example, due to imbalance in optical properties between the target optical path and the background optical path, there may be differences in brightness, color and etc. between the target and the background, but, according to the present invention, no such differences may occur, requiring no adjustments for correcting such differences. In addition, according to the present invention, the arrangement of the apparatus as a whole can be simplified, requiring no combining means which is required for the first prior art. Thus, the present invention can solve the problem seen in the first prior art, as the second prior art.

As described above, however, according to the second prior art, the (upper limit) blinking frequency of the slowly blinking target is too low, which causes a problem of the second prior art that it cannot achieve a reliable ophthalmologic examination contributing to early discovery of glaucoma in particular. In order to solve this problem residing in the second prior art, according to the present invention, the light-emitting means including the plural light-emitting devices is arranged such that the brightness of each of the plural light-emitting devices can be controllable independently from and in parallel with each other. The control means controls the brightness of each of the light-emitting devices independently from and in parallel with each other. This means that the brightness of each of the light-emitting devices can be individually varied as desired. For example, the brightness can be individually varied at a relatively rapidly. Accordingly, according to the present invention, even when the target is to be made to slowly blink, it is possible to make the target blink at a relatively high frequency, or, in particular, at a frequency higher than the blinking frequency in the second prior art. Thus, a reliable examination contributing to early discovery of glaucoma can be realized, and, thus, the problem seen in the second prior art can be solved. It should be noted, however, that, according to the present invention, the target may blink (i.e. be turned on and off alternately), but also it may be made to flicker (i.e. made to shine bright and dim alternately).

The light-emitting means of the present invention may be a two-dimensional light-emitting diode unit including a plurality of light-emitting diode devices, which are the plurality of light-emitting devices, for example. In particular, the light-emitting means of the present invention may be a matrix-type light-emitting diode unit including a plurality of light-emitting diode devices arranged in a matrix. As described above, the light-emitting diode devices are controlled in brightness in parallel with and independently from each other, and, therefore, may have respective control terminals. Specifically, each of the light-emitting diode devices may have an anode terminal and a cathode terminal. The light-emission control means may be so arranged that they have plural control terminals to be connected to the control terminals of the respective ones of the light-emitting diode devices. It should be noted, however, that, when this arrangement is employed, the more the light-emitting diode devices are used, the number of the control terminals of the light-emission control means increases, which causes the structure of the apparatus as a whole, including these terminals, to become complicated.

In order to keep the structure of the apparatus as a whole simple, the light-emitting diode devices may be divided into an appropriate number of blocks equal to or larger than two. The light-emitting diode devices in each of the blocks are arranged in a matrix comprising plural rows and plural columns. Then, the anode terminals, for example, (or the cathode terminals) in the respective light-emitting diode devices belonging to the same row of the respective blocks are connected together by an associated common row-side input connection terminal, and the cathode terminals (or anode terminals), of the respective light-emitting diode devices belonging to the same column in the respective blocks are connected together by an associated common column-side input connection terminal. The light-emission control means has a plurality of row-side output control terminals (i.e. control terminals from which control signals are provided) to be connected to associated ones of the row-side input control terminals (i.e. control terminals to which the control signals are applied) and a plurality of column-side output control terminals to be connected to associated ones of the column-side input control terminals. The respective light-emitting diode devices of the respective blocks are controlled by means of a known dynamic control system. With this arrangement, the number of the terminals for interconnecting the light-emitting diode devices and the light-emission control means can be reduced, resulting in simplification of the structure of the apparatus as a whole including these terminals. It should be noted, however, that, in this structure, because the respective light-emitting diode devices are dynamically controlled for the respective blocks, it may happen that two or more (or, in particular, all) of the light-emitting diode devices cannot be caused to emit light simultaneously. For such a case, an appropriate design is employed to make it appear as if the two or more light-emitting diode devices were emitting light simultaneously with each other. If the number of light-emitting diode devices in each block is too large, the brightness may be insufficient. In order to avoid such trouble, the number of light-emitting diode devices in each block, or, in other words, the number of the blocks is appropriately determined.

According to the present invention, light-valve means and light-valve control means may be additionally used. The light-valve means includes a plurality of light-valve pixels, which are two-dimensionally arranged to correspond to the light-emitting devices of the light-emitting means. The light-valve means is arranged in such a manner that the image for examination formed by a plurality of light-emitting devices is presented through a plurality of light-valve pixels to the eye to be examined. The transmissivity of light emitted from a plurality of light-emitting devices for presentation of the examination image through a plurality of light-valve pixels is individually controllable. The light-valve control means is arranged to individually control the transmissivity of the light through a plurality of light-valve pixels.

With the above-described arrangement, the image for use in examination formed by a plurality of light-emitting devices is presented to the eye to be examined through a plurality of light-valve pixels. Specifically, light emitted from a plurality of light-emitting devices is transmitted to the eye to be examined through a plurality of light-valve pixels, whereby the image for examination is presented to the eye to be examined. The light transmissivity through a plurality of light-valve means is individually controllable by means of the light-valve control means. The control of the light transmissivity makes it possible to control the brightness of the examination image to be presented to the eye for each location corresponding to each of the plural light-valve pixels. For example, fine adjustment of the brightness of the target and fine adjustment of the background can be made independent from each other. The brightness of the target and the brightness of the background can be separately controlled through control of light intensity (luminosity) of each of the light-emitting devices, or brightness of each of the plural light-emitting devices, but they can be independently controlled finely through control of light transmissivity through the light-valve pixels. This gives a great contribution to realization of highly reliable ophthalmologic examination.

The light-valve means referred to herein may be a liquid crystal shutter using liquid crystal, or more specifically, may be a monochrome transmissive liquid crystal panel. As described above, the light-valve means can individually make fine adjustments to the brightness of, for example, the target and the background. Light-valve means for such use does not require a special high speed operation, and, accordingly, a liquid crystal panel for display devices of which operation speed is restricted because of its refresh rate can be sufficiently used. A liquid crystal panel for display purpose has a considerable number (more than several millions) of light-valve pixels, and, accordingly, it is suitable for use as light-valve means referred to herein.

The light-emission control means may control the brightness of target forming ones of the plural light-emitting devices, or, in other words, the brightness of the target in such a manner that the brightness of the target can vary slowly, or gently. With this control, stimulation of the eye to be examined by the presentation of the target thereto is reduced relative to the stimulation of the eye when the brightness of the target changes rapidly, which results in realization of highly reliable examination of eyes, contributing early discovery of glaucoma.

The light-emission control means may control the brightness of background forming ones of the light-emitting devices, or, in other words, the brightness of the background, in such a manner that the brightness of the background is substantially the same as the highest brightness of the target, whereby the brightness of the target is substantially the same as or lower than the brightness of the background. With this control, stimulation of the eye to be examined by the presentation of the target thereto is reduced relative to the stimulation of the eye when the brightness of the target is higher than brightness of the background, which results in realization of highly reliable examination of eyes, contributing early discovery of glaucoma.

Thus, the present invention is suitable for embodying in a perimeter for measuring a visual field of an eye.

BRIEF DESCRIPTION OF DRAWINGS

FIGS. 2A and 2B are explanatory diagrams showing a schematic arrangement of a matrix-type light-emitting diode unit used in the embodiment shown in FIG. 1.

FIGS. 3A and 3B are explanatory diagrams showing a schematic arrangement of a liquid crystal shutter used in the embodiment shown in FIG. 1.

FIGS. 7A, 7B and 7C are explanatory diagrams showing examples of the examination image presented in the embodiment shown in FIG. 1.

FIGS. 9A, 9B and 9C are explanatory diagrams schematically illustrating the brightness of the examination image.

FIGS. 12A and 12B are explanatory diagrams schematically showing the brightness of the image after being subjected to the processing shown in FIG. 11.

FIGS. 13A and 13B are explanatory diagrams showing another example of the matrix-type light-emitting diode unit useable in the embodiment shown in FIG. 1.

FIGS. 14A, 14B and 14C are an explanatory diagram showing a still other example of the matrix-type light-emitting diode unit with a positional relationship with the liquid crystal shutter.

BEST MODE OF INVENTION

An embodiment of the present invention is described with reference to a perimeter by way of example.

Figure 1:
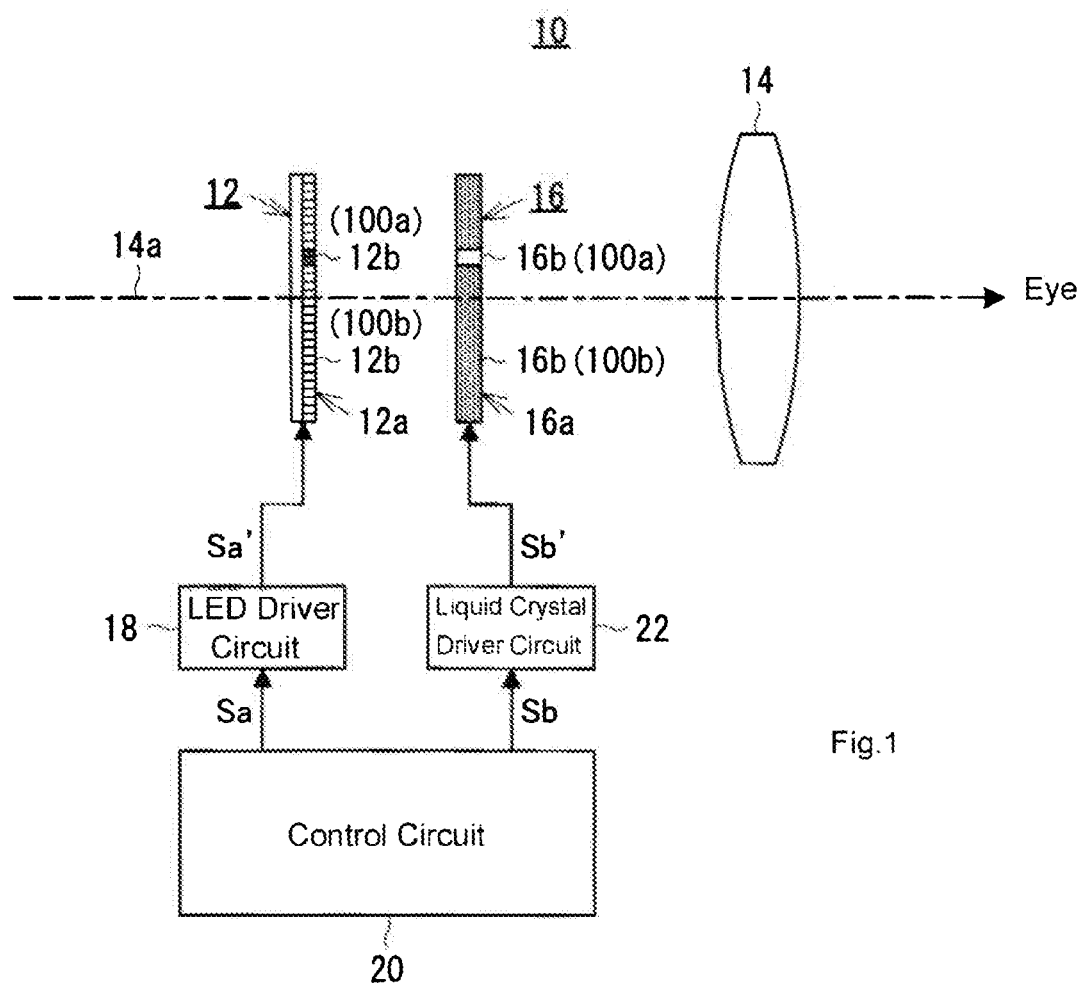
FIG. 1 is an explanatory diagram showing a schematic arrangement of a perimeter according to an embodiment of the present invention.

As shown in FIG. 1, a perimeter 10 according to this embodiment includes, as light-emitting means, a matrix-type light-emitting diode unit (hereinafter referred to as "LED unit") 12. The LED unit 12 has a generally rectangular light-emitting surface 12a, as shown in FIGS. 2A and 2B. The light-emitting surface 12a is formed of a plurality of light-emitting devices, or light-emitting diodes (hereinafter referred to as "LED devices") 12b, 12b, . . . , 12b, of the same specifications arranged in a matrix. The number H of the LED devices 12b arranged in the horizontal direction of the LED unit 12 (i.e. the light-emitting surface 12a) is H=1,920, for example, and the number V of the LED devices 12b arranged in the vertical direction of the LED unit 12 is V=1,080, for example. The shape of LED device 12b, or its front, in particular, (i.e. seen in the direction perpendicular to the surface of FIGS. 2A and 2B) is circular, but it may be generally elliptic or generally rectangular.

Returning to FIG. 1, the LED unit 12 has it light-emitting surface directed toward a later-mentioned main optical system 14 and disposed on an optical axis 14a of the main optical system. More specifically, the LED unit 12 is disposed in such a manner that the optical axis 14a of the main optical system 14 intersects the light-emitting surface 12a of the LED unit 12 at right angles with the optical angle 14a passing through the center of the light-emitting surface 12. A liquid crystal shutter 16 serving as light-valve means is disposed at a location on the optical axis 14a between the LED unit 12 and the main optical system 14.

The liquid crystal shutter 16 is a monochrome transmissive liquid crystal panel for a liquid crystal projector, for example, and has the FHD screen resolution described above. As shown in FIGS. 3A and 3B, the liquid crystal shutter 16 has a generally rectangular screen, or a light-valve surface 16a including layers of liquid crystal etc. stacked between an incidence surface and an emission surface thereof. The light-valve surface 16a is partitioned into a plurality of generally rectangular light-valve pixels (hereinafter referred simply to as "pixel" or "pixels") 16b, 16b, . . . , arranged in a matrix. The number H' of the pixels 16b in the horizontal direction of the liquid crystal shutter 16 (the light-valve surface 16a) is H'=1.920, which is equal to the number H of the LED devices 12b of the LED unit 12 in the same direction. That is, H'=H. The number of the pixels V' in the vertical direction is V'=1,080, which is equal to the number V of the LED devices 12b of the LED unit 12 in the same direction. That is, V'=V. The refresh rate of the liquid crystal shutter 16 is 60 Hz, for example.

Figure 4:
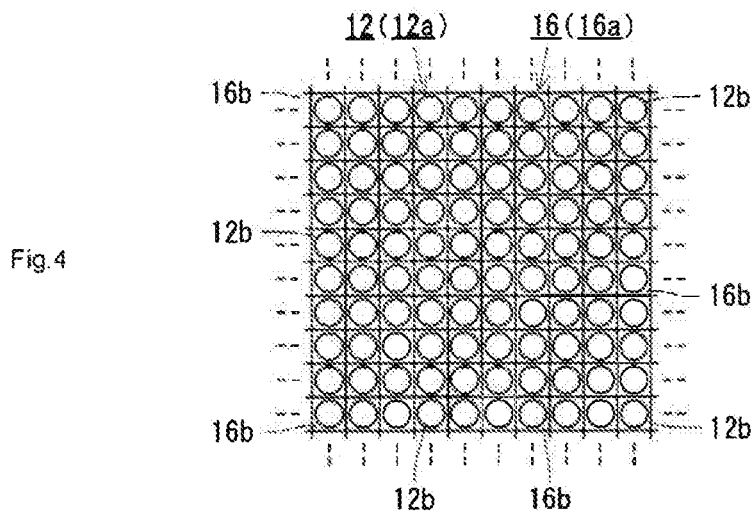
FIG. 4 is an explanatory diagram showing the positional relationship between the matrix-type light-emitting diode unit and the liquid crystal shutter used in the embodiment shown in FIG. 1.

Returning again to FIG. 1, the liquid crystal shutter 16 is disposed between the LED unit 12 and the main optical system 14 in such a manner that the optical axis 14a of the main optical system 14 intersects the light-valve surface 16a of the liquid crystal shutter 16 at right angles and that the optical axis 14a pass through the center of the light-valve surface 16a, as described above. The LED unit 12 and the liquid crystal shutter 16 are disposed relatively near to each other. For example, the LED unit 12 and the liquid crystal shutter 16 are disposed in such a manner that the light-emitting surface 12a of the LED unit 12 and the light-valve surface 16a of the liquid crystal shutter 16 are within the depth of field of the main optical system 14. As shown in FIG. 4, the LED unit 12 and the liquid crystal shutter 16 are disposed in such a manner that the respective ones of the LED devices 12b, 12b, . . . , 12b of the LED unit 12 face the corresponding ones of the pixels 16b, 16b, . . . , 16b of the liquid crystal shutter 16. It should be noted that FIG. 4 shows the LED unit 12 through the liquid crystal shutter 16.

Returning to FIG. 1, the LED unit 12 is connected to a LED driver circuit 18 serving as the driving means dedicated to the LED unit 12. Although not shown in detail in FIG. 1, each of the LED devices 12b, 12b, . . . , 12b has its input control terminals, namely, its own anode terminal and its own cathode terminal. Either the positive electrodes or the negative electrodes of the LED devices 12b, 12b, . . . , 12b may be connected together by means of a common terminal. The respective input control terminals of each LED device 12b are connected to the LED driver circuit 18 independently from the input control terminals of other LED devices 12b, 12b, . . . , 12b. In other words, the LED driver circuit 18 has a plurality of control terminals connected separately to the respective ones of the input control terminals of the respective LED devices 12b, 12b, . . . , 12b. The LED driver circuit 18 generates a LED driving signal Sa' for independently driving the respective LED devices 12b, 12b, . . . , 12b in accordance with a LED control signal Sa provided by a control circuit 20 serving as control means. The LED driving signals Sa' are separately applied to the respective LED devices 12b, 12b, . . . , 12b, or, in other words, applied in parallel to the LED devices 12b, 12b, . . . , 12b, whereby the respective LED devices 12b, 12b, . . . , 12b, operate separately in parallel with each other, or, in other words, operate independently from each other.

The liquid crystal shutter 16 is connected to a liquid crystal driver circuit 22 serving as dedicated driving means. The liquid crystal driver circuit 22 generates liquid crystal driving signals Sb' in accordance with a liquid crystal control signal Sb supplied by the control circuit 20. The liquid crystal driving signals Sb' are applied to the liquid crystal shutter 16 to operate the liquid crystal shutter 16, or, more specifically, to independently control the transmissivities of the respective pixels 16b, 16b, ..., 16b. The transmissivity of each of the pixels 16b, 16b, ..., 16b is renewed at a frequency corresponding to the above-mentioned refresh rate of 60 Hz.

The main optical system 14 is disposed between an imaginary surface, or an image forming surface, on one hand, for forming an image 100 for use in examination described later which contains the light-emitting surface 12a of the LED unit 12 and the light-valve surface 16a of the liquid crystal shutter 16, both being in the field of depth of the main optical system 14, and the eye (or retina) to be examined, on the other hand. The main optical system 14 is disposed in such a manner that the imaginary plane and the eye to be examined are conjugate with each other. Although not shown, the main optical system 14 includes a focus adjusting lens for adjusting the focus of the system 14.

Figure 5:
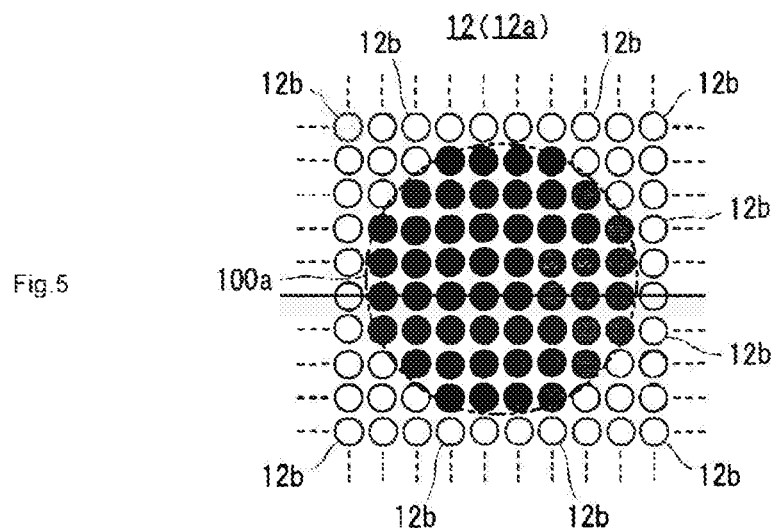
FIG. 5 is an explanatory diagram showing a pattern of a visual target formed by the matrix-type light-emitting diode unit.

The image 100 for use in examination is formed by the above-described image forming surface and formed mainly by the respective LED devices 12b, 12b, ..., 12b of the LED unit 12. Specifically, as shown in FIG. 5, a generally circular visual target 100a is formed by a part of the LED devices 12b, 12b, ..., 12b, and a later-mentioned background 100b which is a region other than the target 100a, is formed by the remaining LED devices 12b, 12b, ..., 12b. The size of the target 100a may be similar to that of a known Goldmann perimeter. In FIG. 5, as for those LED devices 12b which are shown on an alternate long and two short dashes line representing the periphery of the target 100a, LED devices of which more than half is within the area defined by the alternate long and two short dashes line are counted as the ones forming the target 100a, and the other LED devices are counted as the ones forming the background 100b. How the LED devices 12b on the alternate long and two short dashes line should be treated is not limited to the described rule, but can be determined appropriately depending on various conditions including the size of the target 100a.

Figure 6:
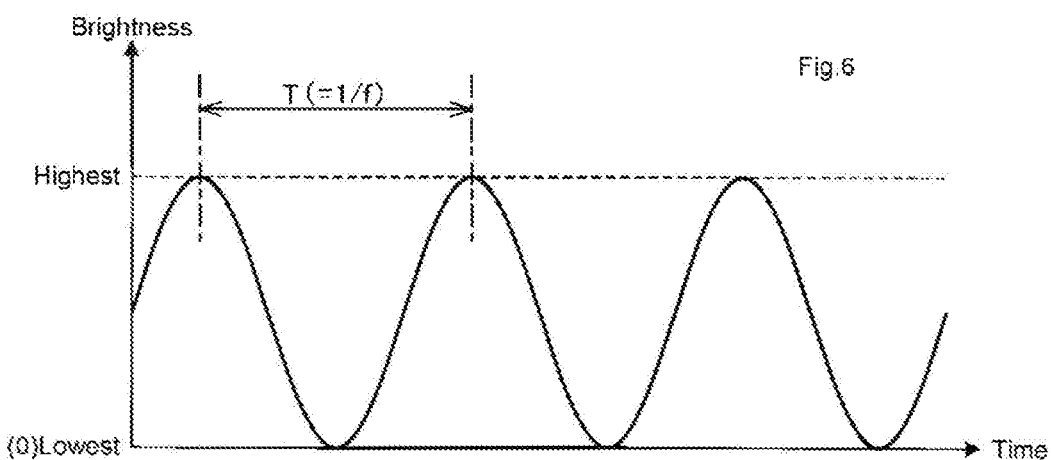
FIG. 6 is an explanatory diagram showing how the light-emitting diode devices are controlled to form the visual target.

Each of the LED devices 12b forming the target 100a is driven to operate to emit light of which brightness (emitted light intensity) varies along a generally sinusoidal waveform as shown, for example, in FIG. 6, in accordance with an associated one of the above-described LED driving signals Sa', to thereby slowly flicker. In FIG. 6, the lowest value of brightness of each LED devices 12b is zero, and, therefore, strictly speaking, each LED device 12b blinks, or is turned on and off. The blinking period T of the LED devices 12b, or the blinking frequency f which is equal to the reciprocal of the blinking period T (=1/T), can be arbitrarily set to a value within a range of from 1 Hz to 200 Hz. The reason why the LED devices 12b can generally sinusoidally blink at such relatively high frequency f is that the LED devices can be independently operable. The highest and lowest values of the brightness of the LED devices 12b can be also set as desired to values within a predetermined range.

As for the LED devices 12b which form the background 100b are driven to emit light with constant brightness equivalent to the highest brightness of the LED devices 12b forming the target 100a. The associated ones of the above-mentioned LED driving signals Sa' are separately applied to the respective LED devices 12 forming the background 100b. The LED control signal Sa for that purpose is generated accordingly.

The liquid crystal shutter 16 operates to provide the highest transmissivity to all of the pixels 16b, 16b, ..., 16b of the light-valve surface 16a thereof. In other words, the liquid crystal shutter 16 operates to make all of the pixels 16b, 16b, ..., 16b open. The liquid crystal driving signals Sb' are applied to the liquid crystal shutter 16, and the liquid crystal control signal Sb for that purpose is generated for application to the liquid crystal shutter 16.

With this arrangement, the light emitted from each of the LED devices 12b, 12b, ..., 12b of the LED unit 12 is projected to the eye to be examined through the pixels 16b, 16b, ..., 16b of the liquid crystal shutter 16 and the main optical system 14. The light emitted by the LED devices 12b, 12b, ..., 12b is generally white, unpolarized light, for example. As a result, one of images 100 for examination like the ones shown in FIGS. 7A, 7B and 7C is presented to the eye. The examination image 100 consists of the target 100a and the remaining portion, i.e. the background 100b. The target 100a slowly blinks sinusoidally, and the background 100b maintains constant brightness equal to the highest brightness of the target 100a. FIG. 7A shows the image 100 with the target 100a with the highest brightness, FIG. 7B shows the image 100 with the target 100a with the lowest brightness, and FIG. 7C shows the image 100 at a time during a transition from one of the states shown in FIGS. 7A and 7B to the other. The blinking frequency f of the target 100a is settable, as desired, to a value within a range of from 1 Hz to 200 Hz.

According to this embodiment, the examination image 100 consisting of the target 100a and the background 100b is projected to the eye to be examined. The target 100a slowly blinks sinusoidally, and it is arranged that the blinking frequency f can be set, as desired, to a frequency within a range of 1 Hz to 200 Hz. In this, the present embodiment is generally same as the above-described first prior art (except the upper limit of the blinking frequency f of the target 100a). Accordingly, with the described embodiment, like the first prior art, it is possible to realize a highly reliable examination, which can contribute early discovery of glaucoma. Besides that, according to the described embodiment, it is not necessary to make any positional adjustments as required in the first prior art. According to the first prior art, the target and the background are formed by separate means, and, therefore it is necessary to adjust the positions of these separate means. On the other hand, according to the described embodiment, the target is formed by means of a part of the LED devices 12b, 12b, ..., 12b prearranged in a matrix with the background 100b formed by the remaining LED devices in the matrix, and, therefore, no adjustments required in the first prior art is required. Furthermore, according to the first prior art, there may be some difference in brightness, color etc. between the target and the background due to imbalance in optical characteristic between the paths of the target light and the background light, but, according to the described embodiment of the present invention, since the plural LED devices used for forming the target 100a and the background 100b are of the same specifications, i.e. have the same properties, no differences as seen in the first prior art arise, and, accordingly, no adjustment for correcting them is required. In addition, since any combining means as required by the first prior art is not necessary in the described embodiment of the present invention, the arrangement of the perimeter as a whole can be further simplified. As described in the above, the second prior art requires no adjustments as required in the first prior art, and can simplify the arrangement of the apparatus as a whole relative to the first prior art. However, the second prior art cannot realize a highly reliable ophthalmologic examination contributable to early discovery of glaucoma. On the other hand, the described embodiment of the present invention can realize a highly reliable ophthalmologic examination contributable to early discovery of glaucoma.

The perimeter 10 according to the described embodiment of the present invention does not require troublesome adjustments, has its structure simplified and still can realize a highly reliable examination contributing to early discovery of glaucoma. Thus, the apparatus according to the described embodiment of the invention is free of the problems found in the first and second prior arts and still has the merits the first and second prior arts have.

Figure 8:
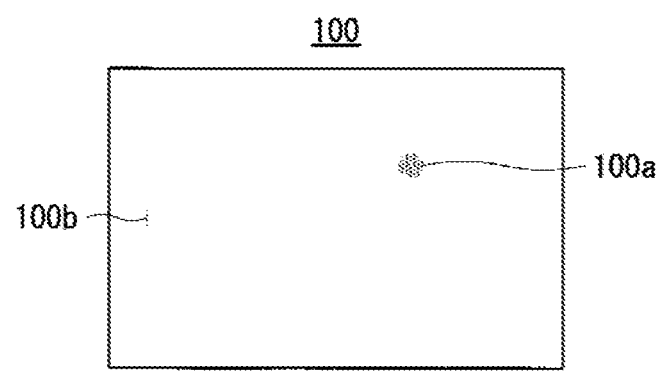
FIG. 8 is an explanatory diagram showing an example of the examination image shown in FIG. 7, illustrating how it is seen to an eye being examined.

According to the described embodiment, depending on the blinking frequency f and the response characteristic of the eyes to be examined, the blinking target 100a may be sometimes seen by the eye as if it were not blinking but were at a constant brightness slightly lower (darker) than the background 100b, as shown in FIG. 8. Such phenomenon may be illustrated in another way as shown in FIGS. 9A, 9B and 9C, for example. When the image 100 shown in FIG. 9A consisting of the target 100a having the highest brightness A same as the brightness of the background 100b and the image 100 shown in FIG. 9B consisting of the target 100a having the lowest brightness of zero (0), far darker than the background 100b, are alternately presented to the eye, the eye may sometimes see the image 100 as if the target 100a were presented to the eye at a constant brightness B, which is slightly darker than the background 100b (i.e. B<A) as shown in FIG. 9C. FIG. 9A shows the state corresponding to the state shown in FIG. 7A, FIG. 9B shows the state corresponding to the state shown in FIG. 7B, and FIG. 9C shows the state corresponding to the state shown in FIG. 8. Such phenomenon may lower the reliability (or the accuracy) of the examination.

Figure 10:
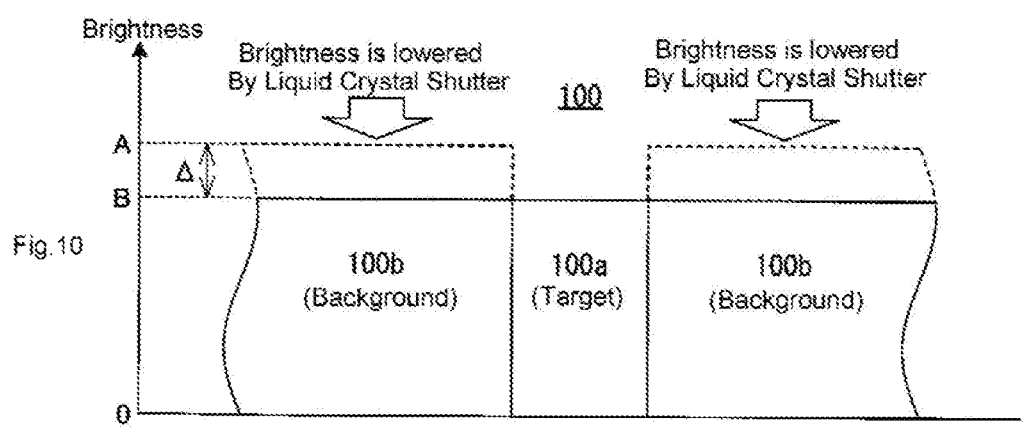
FIG. 10 is an explanatory diagram illustrating a process for removing a problem in the image shown in FIG. 8.

In order to solve this problem, according to the described embodiment of the present invention, as shown in FIG. 10, the brightness of the background 100b is adjusted in such a manner that the brightness of the background 100b in the image 100 being seen by the eye becomes equivalent to the brightness of the target 100a. The lowering of the brightness of the background 100b is done by the liquid crystal shutter 16. Specifically, the transmissivity of the pixels 16b, 16b, ..., 16b of the liquid crystal shutter 16 corresponding to the background 100b is reduced to an appropriate value, whereas the remaining ones (the pixels corresponding to the target 100a) are kept open. Such liquid crystal control signal Sb is generated as to control the liquid crystal shutter 16 to effectuate this operation of the shutter 16. This can prevent the inconvenience shown in FIG. 8, and the reliability of the examination is maintained.

Figure 11:
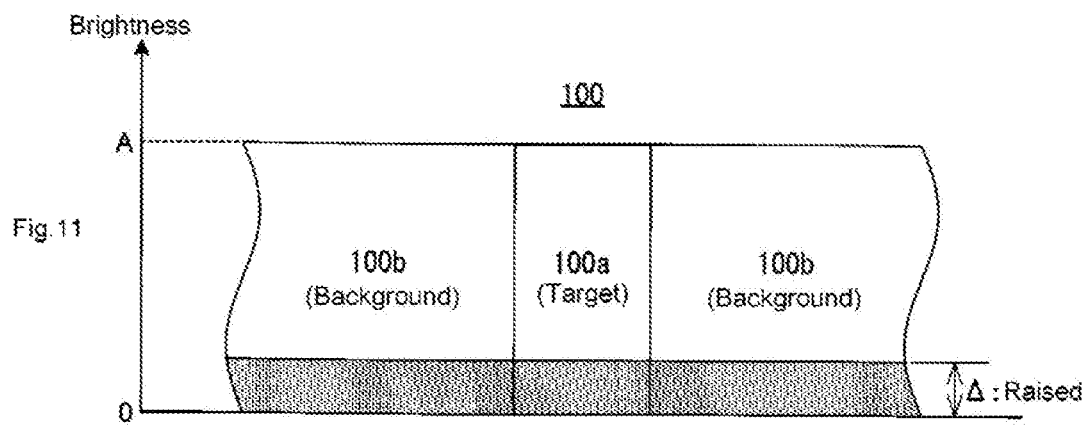
FIG. 11 is an explanatory diagram showing a step following the step shown in FIG. 10.

It should be noted, however, that, in the state shown in FIG. 10, the brightness of the entire image 100 including the target 100a and the background 100b is lowered, or, in other words, the brightness of the image 100 decreases from the original brightness A to brightness B. This is also undesirable. In order to remove this undesirable effect, according to the embodiment being described, the brightness of the image 100 including the target 100a and the background 100b is increased or raised as a whole as shown in FIG. 11. This lifting up of the brightness of the image 100 as a whole is carried out by the LED unit 12. More specifically, the level of the brightness of all of the LED devices 12a, 12a, ..., 12a is raised by an amount equal to the difference $\Delta(=A-B)$ where A is the brightness the image 100 originally has to have and B is the decreased brightness. Such LED control signal Sa is generated to provide such effect, and LED driving signals Sa' corresponding to the thus generated LED control signal Sa are supplied independently to the respective LED devices 12a, 12a, ..., 12a. This makes correction of the entire brightness of the image 100 for use in the examination to the original brightness A, to thereby maintain the reliability of the examination.

With the entire brightness of the image 100 corrected as shown in FIG. 11, when the brightness of the target 100a is presented with the highest brightness, the target 100a is brighter than the background 100b as shown in FIG. 12A. The brightness C of the target 100a in this case is, when calculated roughly, C=A+A where A is the original brightness of the target 100a and $\Delta$ is the above-discussed difference. When the target 100a is presented with the lowest brightness, the target 100a is brighter than brightness of 0 and has a brightness level, which, when calculated roughly, is D ($=\Delta$), which is the raised amount. This may or may not cause some undesirable effect. However, since the brightness C of the target 100a shown in FIG. 12A significantly differs from the brightness D shown in FIG. 12B, and the amount $\Delta$ is considerably smaller than the brightness of the image 100 as a whole and, in particular, smaller than the brightness of the background 100b, there is no fear that such undesirable effect is produced.

The described embodiment is one of the examples in which the present invention is practiced, and the present invention is not limited to it.

For example, considering the LED unit 16, the LED devices 16b, 16b, ..., 16b of the LED unit 16 have their own input control terminals, that is, there are a large number of input control terminals equal to the total number of the LED devices 16b, 16b, ..., 16b (=1,920×1080). Such a LED unit 16 can be realized by applying an IC lamination technique, but the number of the input control terminals is too large. As for the LED driver circuit 18, too, has a plurality of output control terminals to be connected individually to the corresponding input control terminals, or, in other words, has the output control terminals equal in number to the input control terminals of the LED devices 16b, 16b, ..., 16b. Accordingly, the structure of the perimeter 10 including the input control terminals of the LED devices 16b, 16b, ..., 16b and the output control terminals of the LED driver circuit 18 is very complicated. To avoid such drawback, the following structure may be employed.

As shown in FIGS. 13A and 13B, the LED devices 16b, 16b, ..., 16b may be divided into plural blocks 16c, 16c, ..., 16c. Desirably, the LED devices 16b, 16b, ..., 16b in each block 16c may be divided to form a matrix consisting of plural rows and plural columns. FIG. 13A shows an example in which the LED devices are divided by m in the vertical direction of the LED unit 16 (where m is an integer equal to 2 or larger), and n in the horizontal direction (where n is an integer equal to 2 or larger). Then, as shown in FIG. 13B, the anode terminals, for example, of the respective LED devices 16b, 16b, ..., 16b belonging to the same row in each of the same blocks 16c are connected together by a common row-side connection terminal 16d, with the cathode terminals of the LED devices 16b, 16b, ..., 16b belonging to the same column in each of the same blocks 16c connected together by a common column-side input connection terminal 16e. It should be noted that the cathode terminals of the respective LED devices 16b, 16b, ..., 16b belonging to the same row in each of the same blocks 16c are connected together by a common row-side connection terminal 16d, with the anode terminals of the LED devices 16b, 16b, ..., 16b belonging to the same column in each of the same blocks 16c connected together by a common column-side input connection terminal 16e. Although not shown in detail, the LED driver circuit 18 has a plurality of row-side control terminals connected to the respective ones of the row-side connection terminals 16d, 16d, ..., 16d, and a plurality of column-side connection terminals connected to the respective ones of the column-side connection terminals 16e, 16e, ..., 16e. The LED driver circuit 18 controls the LED devices 16b, 16b, 16b of each block by a known dynamic control system. By employing this arrangement, the number of the terminals for connecting the LED devices 16b, 16b, ..., 16b and the LED driver circuit 18 can be reduced, resulting in simplification of the structure of the perimeter 10 as a whole including these terminals With the described arrangement, however, because the respective LED devices 16b, 16b, ..., 16b are dynamically controlled for the respective blocks 16c as described above, it may happen that two or more (or, in particular, all) of the LED devices 16b, 16b, ..., 16b cannot be caused to emit light simultaneously. For such a case, an appropriate design is employed to make it appear as if the two or more LED 16b, 16b, ..., 16b devices were emitting light simultaneously with each other. Furthermore, if the number of LED devices 1b in each block is too large, the brightness of the LED devices may be insufficient. In order to avoid such trouble, the number of LED devices 16b in each block 16c, or, in other words, the number of the blocks 16c (m×n) is appropriately determined.

The LED devices 12b of the LED unit 12 are equal in number to the pixels 16b of the liquid crystal shutter 16, and, as shown in FIG. 4, the LED devices 12b, 12b, ..., 12b of the LED unit 12 and the pixels 16b, 16b, ..., 16b of the shutter 16 are disposed at respective position in one-to-one correspondence with each other. However, the invention is not limited to it. For example, the size of the LED devices 12b of the LED unit 12 is larger than that of the pixels 16b of the liquid crystal shutter 16, in general. Then, as shown in FIGS. 14A, 14B and 14C, plural pixels 16b may be used for one LED device 12b. In other words, the number of the LED devices 12b of the LED unit 12 may be smaller than the number of pixels 16b of the liquid crystal shutter 16. FIG. 14A shows an arrangement in which four (=2×2) pixels 16b face to a single LED device 12b. FIG. 14B shows an arrangement in which sixteen (=4×4) pixels 16b, 16b, ..., 16b are used in correspondence to a single LED device 12b, and FIG. 14C shows an arrangement in which sixty-four (=8×8) pixels 16, 16b, ..., 16b are disposed in correspondence to a single LED device 12b. Contrary to this, the number of the pixels 16b of the liquid crystal shutter 16 can be larger than the number of the LED devices 12b of the LED unit 12.

Figure 15:
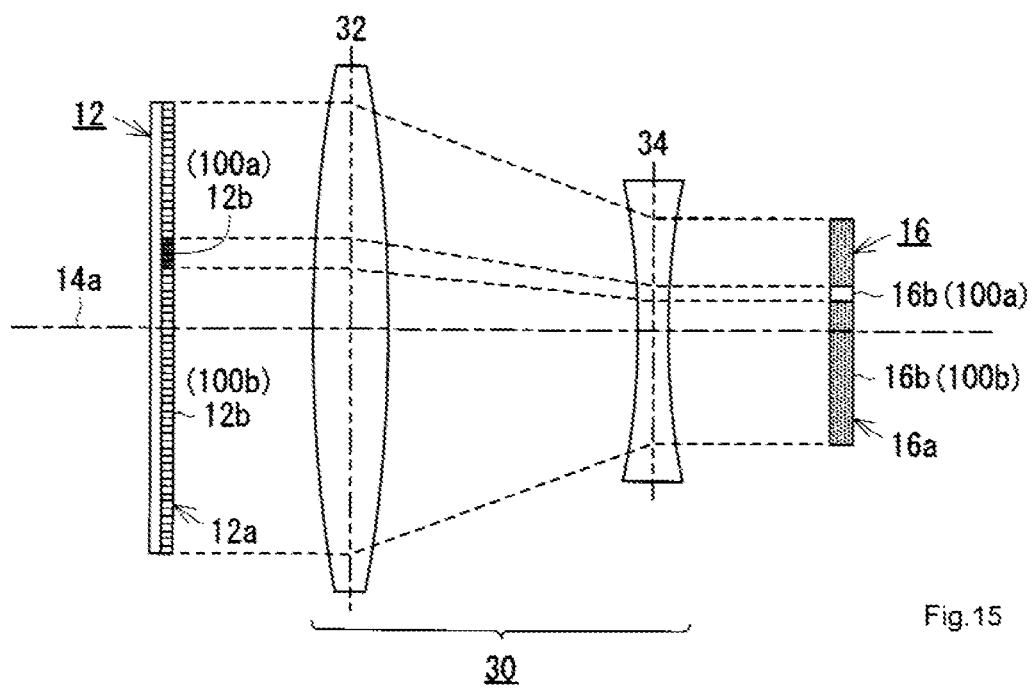
FIG. 15 is an explanatory diagram of another embodiment of the present invention.

As for the liquid crystal shutter 16, there may be a case where its light-valve surface (or screen) 16a, for example, is relatively small in size (i.e. diagonal length) which is around one inch. In such a case, the light-emitting surface 12a of the LED unit 12 usually is larger than the light-valve surface 16a of the liquid crystal shutter 16. In such a case, as shown in FIG. 15, adjusting means 30 may be disposed between the LED unit 12 and the liquid crystal shutter 16 for adjusting the light emitted from the light-emitting surface 12a of the Led unit 12 to match the size of the light-valve surface 16a of the liquid crystal shutter 16. FIG. 5 shows an example of the adjusting means 30 including a converging lens group 32 and a diverging lens group 34.

As the liquid crystal shutter 16, one having a relatively large-sized (larger than or equal to ten inches) light-valve surface 16a may be used with the LED unit 12 having its light-emitting surface 12a equivalent in size to the light-valve surface. The LED unit 12 and the liquid crystal shutter 16 are disposed relatively close to each other, or, to put it in extreme terms, disposed in intimate contact with each other.

With this arrangement employed, without using the main optical system 14 described above, examination of the visual field can be realized through direct observation of (the image forming surface provided by) the LED unit 12 and the liquid crystal shutter 16. Because the main optical system 14 is removed, the structure of the examination apparatus can be further simplified.

The light-emitting means used in the described embodiment is the matrix-type LED unit 12 having a plurality of LED devices 12b, 12b, ..., 12b are arranged in a matrix, but the light-emitting means is not limited to a matrix-type one. The LED devices 12b, 12b, ..., 12b may be arranged in a generally honeycomb shaped array. Further, the LED devices 12b is not limited to white, but they may be color LED devices. The light-emitting means may be an EL (electroluminescence) display, in particular, an organic EL display and other one.

The visual target 100a has been described as being generally circular, but it may be polygonal, e.g. triangular and rectangular. They may be rod-shaped, loop-shaped or any other shape. It may be arranged that a plurality of visual targets 100a are simultaneously presented. Although the target 100a has been described as having generally sinusoidally varying brightness, or, in other words, flickering (or blinking), the brightness of the visual target 100a may vary along a generally sawtooth wave or triangularly.

The background 100b has been described as having constant brightness equivalent to that of the visual target 100a when the target 100a is the brightest (except for the case shown in FIGS. 12A and 12B). However, it may be arranged that the LED devices 12b associated with the background 100b are turned off whereby the background 100b is presented dark. In other words, the background 100b may be presented with brightness lower than that of the visual target 100a. It should be noted, however, that, as described with reference to the embodiment above, by employing a constant brightness for the background 100b, which constant brightness is equal to the brightness of the visual target when it is brightest, the stimulation of the eye being examined by the presentation of the target 100a is restricted, resulting in high reliability of the examination.

As described above, the liquid crystal shutter 16 serving as the light-valve means functions to restrict the brightness of the background 100b, or, in other words, functions to make fine-adjustment of the brightness of the background 100b. The liquid crystal shutter 16 can make fine-adjustment of the brightness of the background 100b but also can do fine adjustment of the target 100a. The liquid crystal shutter 16 can make fine-adjustment of the brightness of the target 100a and the background 100b independent of each other. Considering that the brightness of the visual target 100a and the brightness of the background 100b can be controlled by controlling the intensity of the light emitted by the LED devices 12b, 12b, ..., 12b providing the target 100a and the background 100b, respectively, the fact that the brightness of the target 100a and the brightness of the background 100b can be adjusted separately from the fine-adjustment of the intensity of light emitted from the LED devices 12b contributes greatly the realization of highly reliable ophthalmologic examination.

The liquid crystal shutter 16 largely contributes to improvement of the picture quality of the examination image 100 including the visual target 100a and the background 100b. For example, the image 100 for use in examination may show irregularities in brightness due to differences in properties of the LED devices 12b, 12b, ..., 12b, but such brightness irregularities can be removed by individually controlling the transmissivities of the respective pixels 16b, 16b, ..., 16b of the liquid crystal shutter 16, whereby the picture quality of the examination image 100 can be improved. For such use, a liquid crystal shutter having its operation speed restricted due to its refresh rate can be adequately used as the light-valve means in the present invention.

The light valve means is not limited to the light-transmissive liquid crystal shutter 16, but a light-reflective liquid crystal shutter, for example, may be used. When the light-reflective liquid crystal shutter is used, the light emitted from the LED unit 12 is reflected by the light-reflective liquid crystal shutter, and the reflected light is projected through the main optical system 14 onto the eye being examined. An electronic optical device called "micro mirror device", which includes a number of micro mirrors are arranged in a two-dimensional array, may be employed as light-valve means. When a micro mirror device is used, the light emitted by the LED unit 12 is reflected from the micro mirror device onto the eye being examined through the main optical system 14.

The perimeter 10 described above as an embodiment of the invention is used in static perimetry, but the present invention can be embodied in a perimeter used in kinetic perimetry, too. Further, the present invention is applicable not only to a perimeter, but also to other ophthalmologic examination apparatuses.

EXPLANATION OF REFERENCE NUMERALS

10: Perimeter
12: LED Unit
12b: LED Devices
18: LED Driver Circuit
20: Control Circuit
100: Image
100a: Visual Target
100b: Background

The invention claimed is:

1. An ophthalmologic examination apparatus for presenting an image for examination including a flickering visual target to an eye to be examined and examining said eye on the basis of how said eye recognizes said target, comprising:
light-emitting means including a plurality of light-emitting devices of the same specifications two-dimensionally disposed to form said image, said plurality of light-emitting devices being controllable in brightness independently from and in parallel with each other; and
light-emission control means controlling the brightness of said plurality of light-emitting devices in parallel with and independently from each other;
said light-emission control means performing control in such a manner that a part of said plurality of light-emitting devices flicker to thereby form said visual target of said image and that the remaining part of said light-emitting devices have a constant brightness to thereby form said background, which is a region of said image other than said part.

2. The ophthalmologic examination apparatus according to claim 1, wherein said light-emitting means is a two-dimensional light-emitting diode unit comprising a plurality of light-emitting diode devices.

3. The ophthalmologic examination apparatus according to claim 1, further comprising:
light-valve means including a plurality of two-dimensionally disposed light-valve pixels, said image formed by said plurality of light-valve pixels being presented to said eye to be examined through said plurality of light-valve pixels, the transmissivity of said plurality of light-valve pixels for the light emitted from said plurality of light-emitting devices projected to said eye to be examined being independently controllable; and
light-valve control means for separately controlling said transmissivity of said plurality of light-valve pixels.

4. The ophthalmologic examination apparatus according to claim 3, wherein said light-valve means is a liquid crystal shutter including said plurality of light-valve pixels using liquid crystal.

5. The ophthalmologic examination apparatus according to claim 1, wherein said light-emission control means makes such control that the brightness of that part of said light-emitting devices which form said visual target slowly changes.

6. The ophthalmologic examination apparatus according to claim 1, wherein said light-emission control means makes such control that the brightness of said remaining part of said plurality of light-emitting devices which form said background is substantially same as the brightness of said visual target forming devices when said visual target forming devices are brightest.

7. The ophthalmologic examination apparatus according to claim 1, wherein said apparatus is a perimeter for measuring the visual field of said eye to be examined.

* * * * *